(12) United States Patent
Duckett, III et al.

(10) Patent No.: US 11,298,003 B2
(45) Date of Patent: Apr. 12, 2022

(54) SMART COUPLING SYSTEM FOR MEDICAL INSTRUMENTS

(71) Applicant: KARL STORZ Imaging, Inc., Goleta, CA (US)

(72) Inventors: George E. Duckett, III, Castaic, CA (US); Daniel Lietz, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 405 days.

(21) Appl. No.: 16/218,190

(22) Filed: Dec. 12, 2018

(65) Prior Publication Data

US 2020/0187758 A1    Jun. 18, 2020

(51) Int. Cl.
 *A61B 1/00* (2006.01)
 *A61B 1/04* (2006.01)
 *A61B 90/98* (2016.01)

(52) U.S. Cl.
 CPC ...... *A61B 1/00114* (2013.01); *A61B 1/00121* (2013.01); *A61B 1/042* (2013.01); *A61B 1/00105* (2013.01); *A61B 90/98* (2016.02)

(58) Field of Classification Search
 CPC . A61B 1/00114; A61B 1/042; A61B 1/00105; A61B 1/00112; A61B 1/00124; A61B 90/90; H01R 13/62; H01F 38/14
 See application file for complete search history.

(56) References Cited

U.S. PATENT DOCUMENTS

| | | | |
|---|---|---|---|
| 3,144,527 A | 8/1964 | Tolegian | |
| 7,311,526 B2 | 12/2007 | Rohrbach | |
| 7,351,066 B2 | 4/2008 | DiFonzo | |
| 7,641,477 B2 | 1/2010 | DiFonzo | |
| 7,841,776 B2 | 11/2010 | DiFonzo | |
| 8,177,560 B2 | 5/2012 | Rohrbach | |
| 8,343,042 B2 | 1/2013 | Leiner | |
| 8,497,753 B2 | 7/2013 | DiFonzo | |
| 8,576,034 B2 | 11/2013 | Bilbrey | |
| 8,894,420 B2 | 11/2014 | Schichl | |
| 8,970,332 B2 | 3/2015 | DiFonzo | |
| 9,634,428 B2 | 4/2017 | DiFonzo | |
| 2004/0209489 A1 | 10/2004 | Clapper | |

(Continued)

FOREIGN PATENT DOCUMENTS

| EP | 1721568 A1 | 11/2006 |
|---|---|---|
| EP | 1645219 B1 | 11/2016 |

OTHER PUBLICATIONS

Sigurd, Karin; Extended European Search Report, dated Apr. 28, 2020, pp. 1-9, Munich Germany, Application No. 19215849.1-1122.
Magsafe, Wikpedia https://en.wikipedia.org/wiki/MagSafe.

*Primary Examiner* — Timothy J Neal

(74) *Attorney, Agent, or Firm* — Michael J. Loi

(57) ABSTRACT

A control system for a coupling an input device and an input module of an imaging system for a medical procedure includes a compatibility module and a magnetic force module. The compatibility module generates a compatibility signal indicating the input device is compatible with the input module or indicating that the input device is incompatible with the input module based on electronic information stored on the input device. The magnetic force module that generates a magnetic force between a connector of the input device and a receptacle of the input module based on the compatibility signal.

9 Claims, 6 Drawing Sheets

(56) References Cited

U.S. PATENT DOCUMENTS

| | | |
|---|---|---|
| 2006/0287576 A1 | 12/2006 | Tsuji et al. |
| 2012/0209061 A1 | 8/2012 | Kato |
| 2014/0099808 A1* | 4/2014 | McClelland ....... H01R 13/6205 |
| | | 439/153 |
| 2014/0128674 A1 | 5/2014 | Wieters |
| 2016/0128549 A1 | 5/2016 | Juergens |
| 2017/0172400 A1* | 6/2017 | Shimomura ....... A61B 1/00013 |
| 2017/0264045 A1* | 9/2017 | Eslava ................. G02B 6/3886 |
| 2017/0264046 A1* | 9/2017 | Szeto .................... H01R 11/30 |

* cited by examiner

SMART COUPLING SYSTEM FOR MEDICAL INSTRUMENTS

FIELD

The present disclosure relates to coupling systems for medical instruments including medical video imaging systems and endoscopes.

BACKGROUND

Various medical instruments including electrical components require connectors and receptacles between the instruments and their respective control modules. Endoscopic instruments that make use of either integrated imagers (known as video endoscopes) or camera heads adapted to couple with their proximal ends may, in particular, have a number of couplers, cables, and the like in order to provide illumination, data transfer, commands, power, etc. to the instruments.

The connectors often are located at the terminal end of a cable coupled to the instrument. The cables and instruments in many cases must be able to withstand high temperature cleaning in an autoclave, chemical cleaning, and/or ultraviolet radiation in order to be reusable between medical procedures. The connectors come in a variety of shapes and sizes and include projections, notches, and other mechanical features for engaging with and mating with similar but opposite features of the receptacles. These mechanical features may include frictional couplings, interference couplings, and the like.

The connectors and receptacles typically include exposed metal terminals that may be comprised of gold or other precious metals that resist oxidation and provide low resistance connections. The terminals may provide additional friction for the coupling. However, the terminals frequently engage and disengage when the connector is removed and inserted into the receptacle causing wear and tear over time that may lead to faulty electrical connection and decreased friction or interference fit coupling forces.

The connectors and receptacles typically include many edges, corners, "nooks" and "crannies," and other areas that may collect debris from either the surgery, such as fluids or tissue, or the environment, such as condensation, dust, etc. These areas may need to be thoroughly cleaned and/or sterilized according to government and medical guidelines, which can be costly and time consuming. If not properly cleaned, the debris may further cause the instruments to function improperly due to poor electrical connections.

SUMMARY

A control system for a coupling an input device and an input module of an imaging system for a medical procedure includes a compatibility module and a magnetic force module. The compatibility module generates a compatibility signal indicating the input device is compatible with the input module or indicating that the input device is incompatible with the input module based on electronic information stored on the input device. The magnetic force module that generates a magnetic force between a connector of the input device and a receptacle of the input module based on the compatibility signal.

In other features, the magnetic force module applies a first attractive level of the magnetic force when the compatibility signal indicates compatible and a first repelling level of the magnetic force when the compatibility signal indicates incompatible.

In yet other features, an active procedure module generates an active procedure signal indicating the medical procedure is active or indicating the medical procedure is no longer active based on at least one of a user input and image data generated by the input device. The magnetic force module applies a second attractive level of the magnetic force when the active procedure signal indicates active.

In still other features, a connection monitor generates a connection signal indicating the connector and the receptacle are in a connected state or the connector and the receptacle are in a disconnected state. The magnetic force module applies the first attractive level of the magnetic force when the connection signal indicates a disconnected state. The magnetic force module applies a second attractive level of the magnetic force that is greater than the first attractive level when the connection signal indicates a connected state.

In other features, a timing module increments a timer when the connection signal indicates a disconnected state. After indication of a disconnected state, the magnetic force module increases from the first attractive level to the second attractive level when indication of a subsequent connected state occurs and the timer is less than a predetermined threshold.

In yet other features, the compatibility module includes an RFID reader chip and the electronic information is stored on an RFID tag chip of the connector such that the RFID reader chip powers the RFID tag chip using radio wave energy to transmit electronic information. In still other features, the input device is one of a video camera for an endoscope and a video endoscope.

A coupling system for coupling an input device and an input module of a medical imaging system includes a connector, a receptacle, and a control system. The connector, disposed at a terminal end of a cable of the input device, includes one or more connector magnets and an RFID tag chip. The connector terminates in a planar surface without exposed terminals. The receptacle, disposed within the input module, includes one or more receptacle magnets and an RFID reader chip, the receptacle terminating in a planar surface without exposed terminals. The control system includes a compatibility module and a magnetic force module. The compatibility module generates a compatibility signal indicating the input device is compatible with the input module or indicating that the input device is incompatible with the input module based on electronic information stored on the RFID tag chip. The magnetic force module generates a magnetic force in the one or more receptacle magnets based on the compatibility signal.

In other features, the magnetic force module applies a first attractive level of the magnetic force when the compatibility signal indicates compatible and a first repelling level of the magnetic force when the compatibility signal indicates incompatible.

In yet other features, an active procedure module generates an active procedure signal indicating the medical procedure is active or indicating the medical procedure is no longer active based on at least one of a user input, image data generated by the input device, an IMU, and an accelerometer. The magnetic force module applies a second attractive level of the magnetic force when the active procedure signal indicates active.

In still other features, a connection monitor generates a connection signal indicating the connector and the receptacle are in a connected state or the connector and the receptacle are in a disconnected state. The magnetic force module applies the first attractive level of the magnetic force when the connection signal indicates a disconnected state. The magnetic force module applies a second attractive level of the magnetic force that is greater than the first attractive level when the connection signal indicates a connected state.

In other features, a timing module increments a timer when the connection signal indicates a disconnected state. After indication of a disconnected state, the magnetic force module increases from the first attractive level to the second attractive level when indication of a subsequent connected state occurs and the timer is less than a predetermined threshold.

In yet other features, the compatibility module includes an RFID reader chip and the electronic information is stored on an RFID tag chip of the connector such that the RFID reader chip powers the RFID tag chip using radio wave energy to transmit electronic information.

In other features, the input device is one of a video camera for an endoscope and a video endoscope.

A method for a coupling an input device and an input module of an imaging system for a medical procedure includes placing a connector of a terminal end of a cable connected to the input device in proximity to a receptacle of the input module; generating a compatibility signal indicating the input device is compatible with the input module or indicating that the input device is incompatible with the input module based on electronic information stored in an RFID tag chip of the connector; and generating a magnetic force between the connector of the input device and the receptacle of the input module based on the compatibility signal.

In other features, the method includes generating a first attractive level of the magnetic force when the compatibility signal indicates compatible and a first repelling level of the magnetic force when the compatibility signal indicates incompatible.

In yet other features, the method includes generating an active procedure signal indicating the medical procedure is active or indicating the medical procedure is no longer active based on at least one of a user input and image data generated by the input device; and generating a second attractive level of the magnetic force when the active procedure signal indicates active.

In still other features, the method includes generating a connection signal indicating the connector and the receptacle are in a connected state or the connector and the receptacle are in a disconnected state; generating the first attractive level of the magnetic force when the connection signal indicates a disconnected state; and generating a second attractive level of the magnetic force that is greater than the first attractive level when the connection signal indicates a connected state.

In other features, the method includes incrementing a timer when the connection signal indicates a disconnected state; and increasing from the first attractive level to the second attractive level when indication of a subsequent connected state occurs and the timer is less than a predetermined threshold.

In yet other features, an RFID reader chip of the receptacle powers the RFID tag chip using radio wave energy to transmit electronic information.

DETAILED DESCRIPTION

Figure 1:
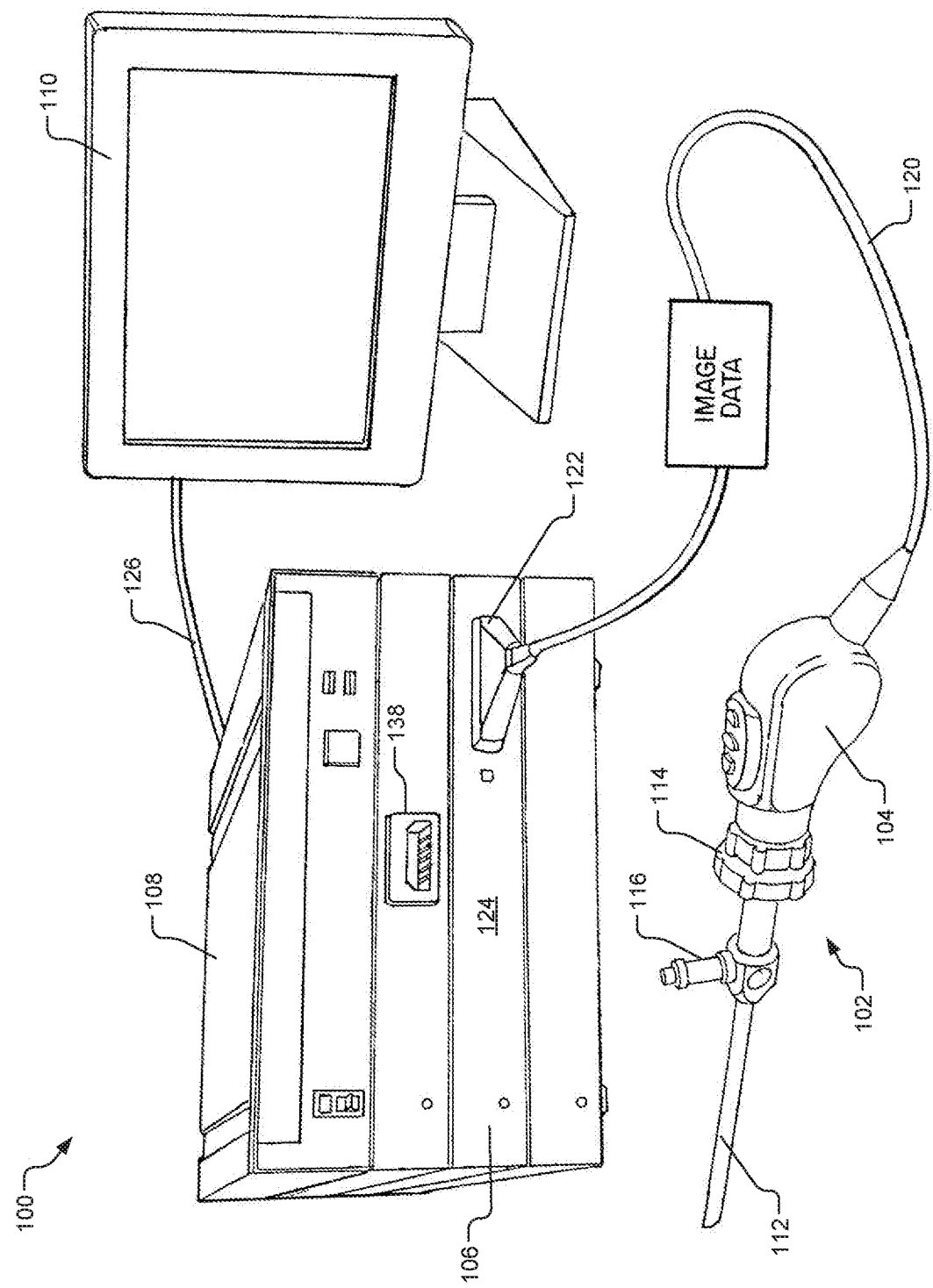
FIG. 1 is a perspective view of medical imaging system featuring a prior art coupling system for a medical video imaging system and endoscope.

The smart coupling system for medical instruments of the present disclosure provides a connector, a receptacle, and control system that reduces risks associated with traditional connectors and receptacles mentioned above. Completely enclosed electronics that use wireless and/or optical data transmission between the connector and receptacle eliminate the need for metal terminals, eliminating wear and tear issues. Smooth, planar surfaces make cleaning and sterilization simpler and more effective by eliminating areas that collect debris. Magnetic forces may be used to provide various levels of magnetic coupling between the connector and the receptacle, reducing the need for mechanical features that rely upon frictional or interference fit to secure the coupling. Control features sense or detect user input, connection status, and compatibility of devices to adjust the magnetic forces for various conditions.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module refers to an application specific integrated circuit (ASIC), a field programmable gate array (FPGA), an electronic circuit, a processor (shared, dedicated, or group) and memory that execute one or more software or firmware programs, a combinational logic circuit, or other suitable components that provide the described functionality.

Referring now to FIG. 1, an exemplary medical imaging system 100 may include an endoscope 102, a camera head 104, one or more input modules 106, a display module 108, and a display unit 110. In the present example, the endoscope 102 includes at a distal end, an elongated shaft 112 for insertion into the body of a patient and at a proximal end, a coupler 114 for coupling with the camera head 104. A light port 116 may be included for receiving light from a light source (not shown) via a light cable (not shown) as is known in the art. The light may exit from the distal end of the endoscope 102 to provide illumination within the body. A series of lenses are housed within the endoscope 102. The camera head 104 may include additional lenses as well as an imager (not shown) for receiving reflected or emitted light from within the body via the lenses of the endoscope 102. In other examples, the endoscope 102 and the camera head 104 may be combined into a single video endoscope that may include the imager at the distal end of the shaft 112 with a handle portion in place of the camera head 104.

The imager generates data that passes down a cable 120 that links the camera head 104 and the input module 106. The cable 120 includes a plurality of wires, typically copper wires, which may transmit image data from the input module 106. The cable 120 may transmit power and commands to the camera head 104. The cable 120 terminates in a connector 122 that is configured to plug into an opening in the operator-facing side 124 of the input module 106. The data may be processed by the input module 106 and further passed along in a processed format to the display module 108. The display module 108 may include various user inputs such as a keyboard, mouse, or other peripheral devices to aid the operator in setting and using the imaging system 100. The display module 108 further delivers a processed image stream to the display unit 110 via display cable 126 for display to the operator.

Figure 2A:
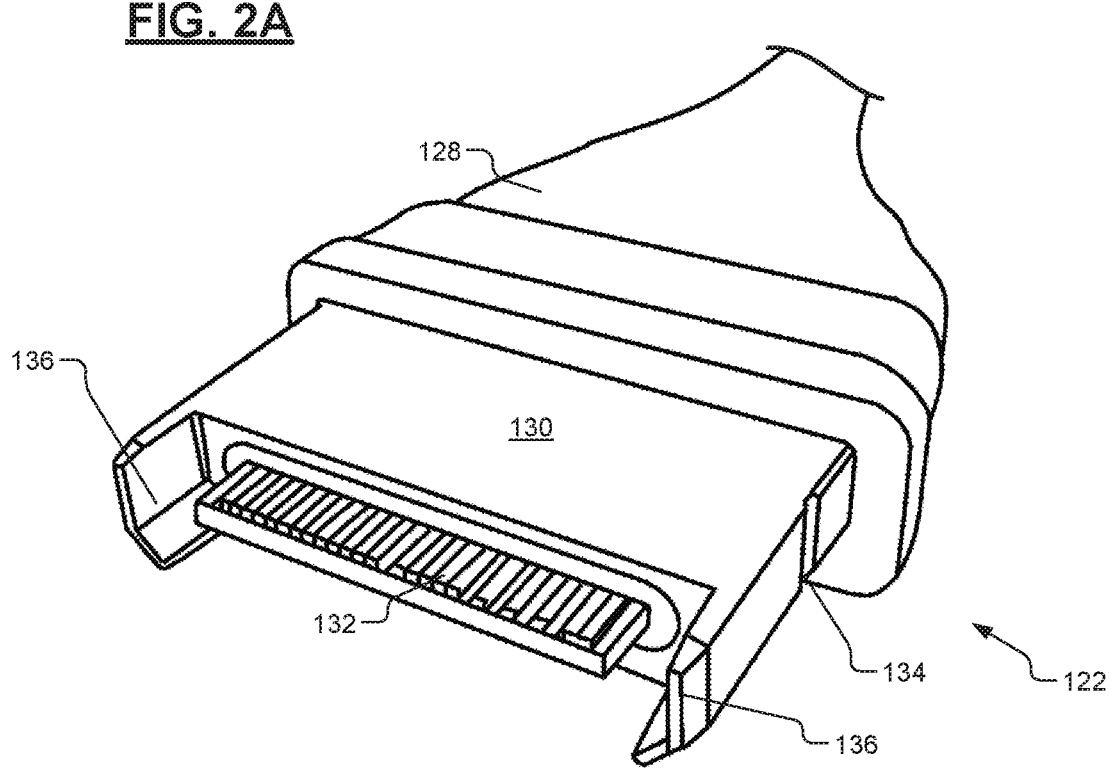
FIG. 2A is a perspective view of a connector of the prior art coupling system of FIG. 1.

Referring now to FIG. 2A, a typical connector 122 includes a rubber housing 128, a metal plug 130, and a plurality of metallic terminals 132. The rubber housing 128 and metal plug 130 may contain a number of electrical connections and components therein which may further be potted in a thermoplastic or silicone rubber to resist shock and vibration. The metal plug 130 may include notches 134, keyed projections 136, and other features that engage mating features on the receptacle 138 of the input module 106. The terminals 132 may engage mating terminals (not shown) of the receptacle 138 to facilitate transfer of power, image data, commands, and the like as is known in the art.

Because the connector 122 is molded with the cable 120 that is connected in turn to the camera head 104, the connector 122 typically requires sterilization between every surgical procedure. Sterilization may include high pressure and high temperature steam cleaning in an autoclave, chemical sterilization, or ultraviolet sterilization. All of these methods of sterilization cause excessive wear and tear on the connector 122. Various exposed portions of the connector 122 receive the most abuse. Furthermore, plugging and unplugging the connector 122 with the receptacle 138 causes wear and tear on the metallic terminals 132, notches 134, and keyed projections 136 resulting in poor electrical contact and/or loose physical coupling.

Figure 2B:
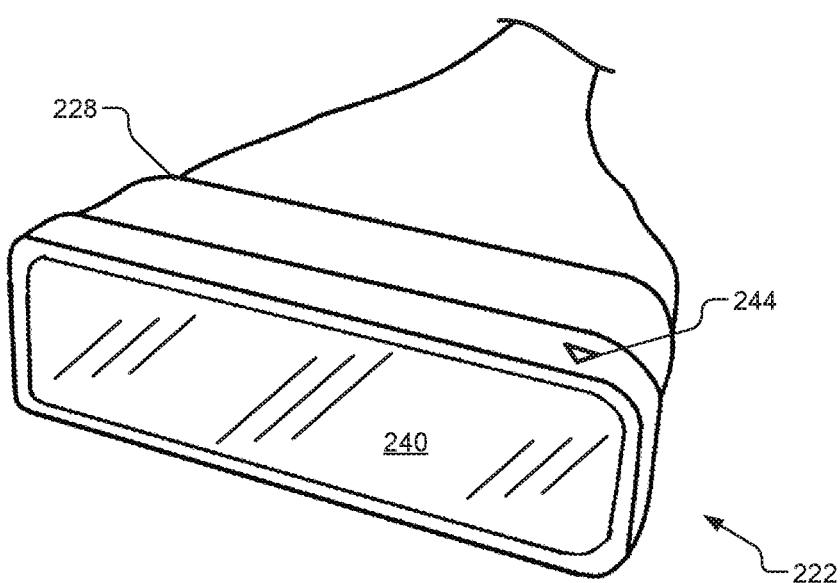
FIG. 2B is a perspective view of a connector of an exemplary smart coupling system according to the principles of the present disclosure.
Figure 3:
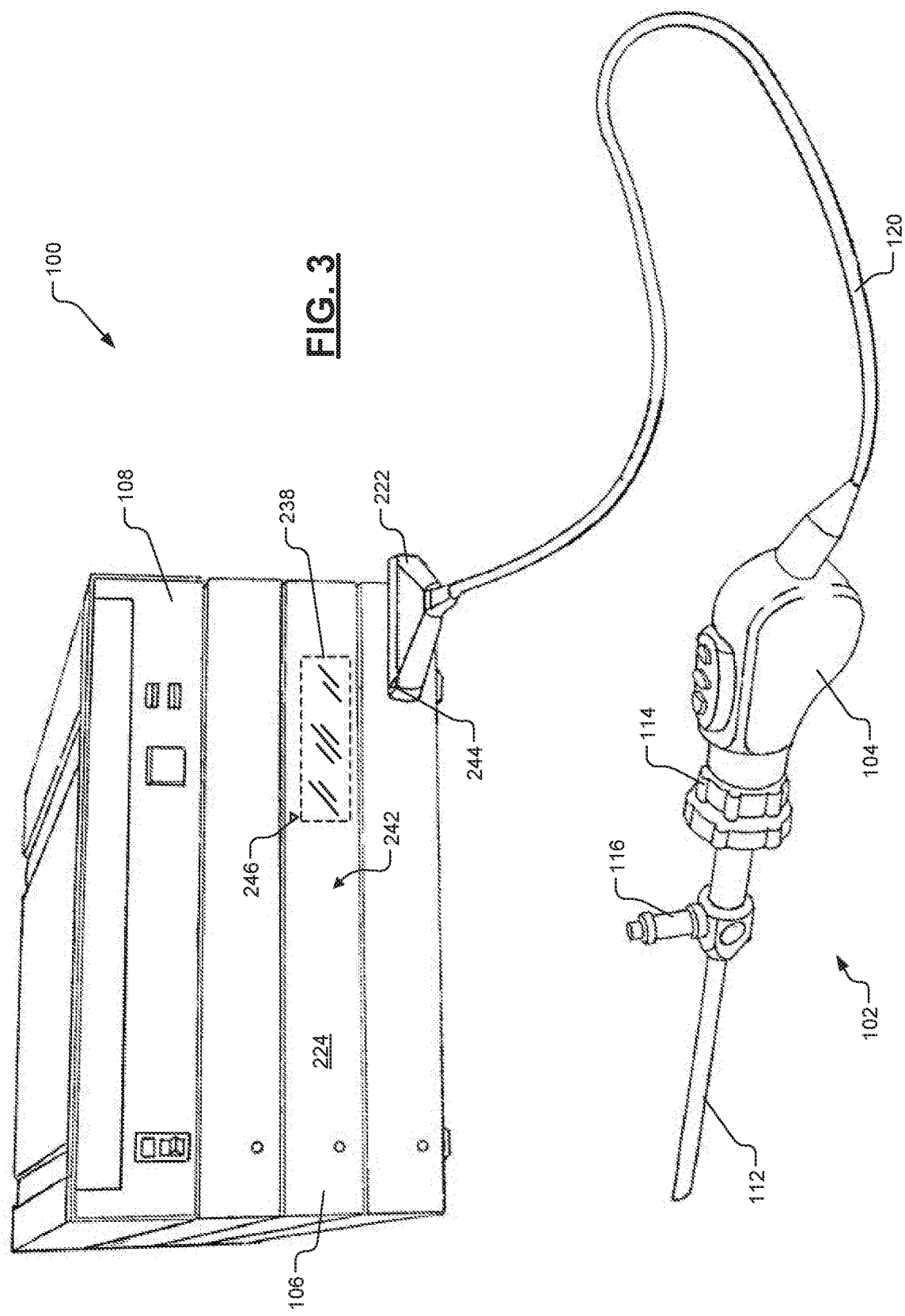
FIG. 3 is a perspective view of the smart coupling system according to the principles of the present disclosure.

FIG. 2B illustrates a fully sealed connector 222 according to the principles of the present disclosure. Connector 222 includes a planar surface 240 that may include a glass or sapphire construction which is configured to engage the receptacle 238. Behind the planar surface 240 and sealed within housing 228 are additional components that will be described in further detail below. Continuing now also with FIG. 3, the imaging system 100 may include a input module 106 with a planar surface 242 on operator-facing side 224 of the input module 106. The planar surface 242 may include a receptacle 238 configured to receive the connector 222. The connector 222 and receptacle 238 may include markings to aid in alignment. For example, the connector may include a first direction indicator 244 and receptacle 238 may include a second direction indicator 246. Alternatively, matching corners may be numbered or provided with a single mark or color indicating proper alignment. In other features, the connector 222 may include permanent magnets that may interact with permanent magnets of the receptacle 238 as will be described below as well.

Figure 4:
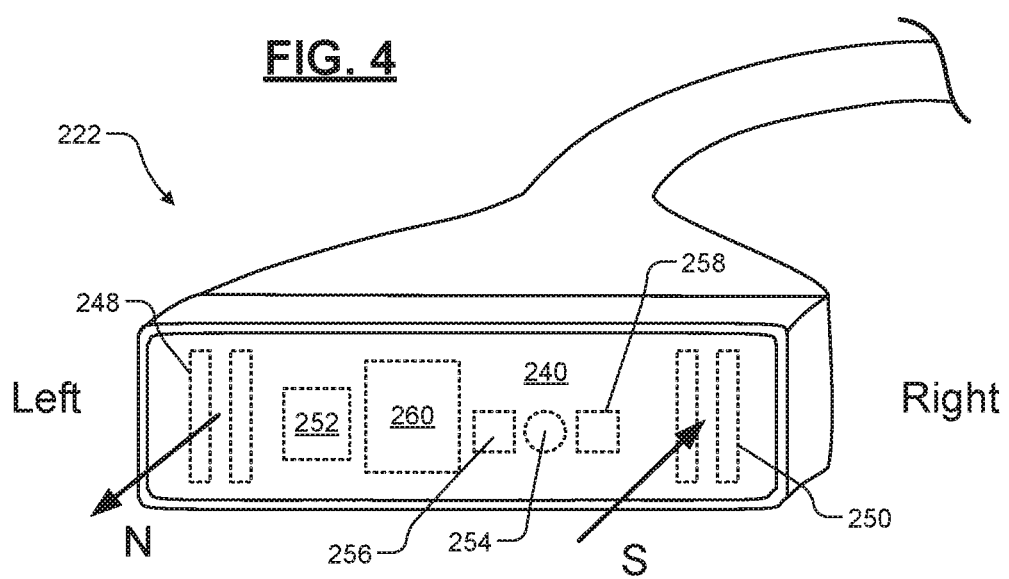
FIG. 4 is another perspective view of the connector of FIG. 2B illustrating additional features of the smart coupling system.

Referring now to FIG. 4, the connector 222 includes one or more connection features behind planar surface 240. The connection features may provide one or more levels of coupling force, facilitate transmission of image sensor data, facilitate transmission of control signals, facilitate transmission of power, and more. In some embodiments, the connector 222 includes a fiber optic coupling for transmission of light from a light source (not shown). In some embodiments, the connector 222 may include permanent magnets, electromagnets, optical channels, inductive power couplings, RFID chips, short-range wireless transmitters/receivers, and similar adjustable attractive force, communication, and power delivery features that may be concealed behind the planar surface 242.

Figure 5:
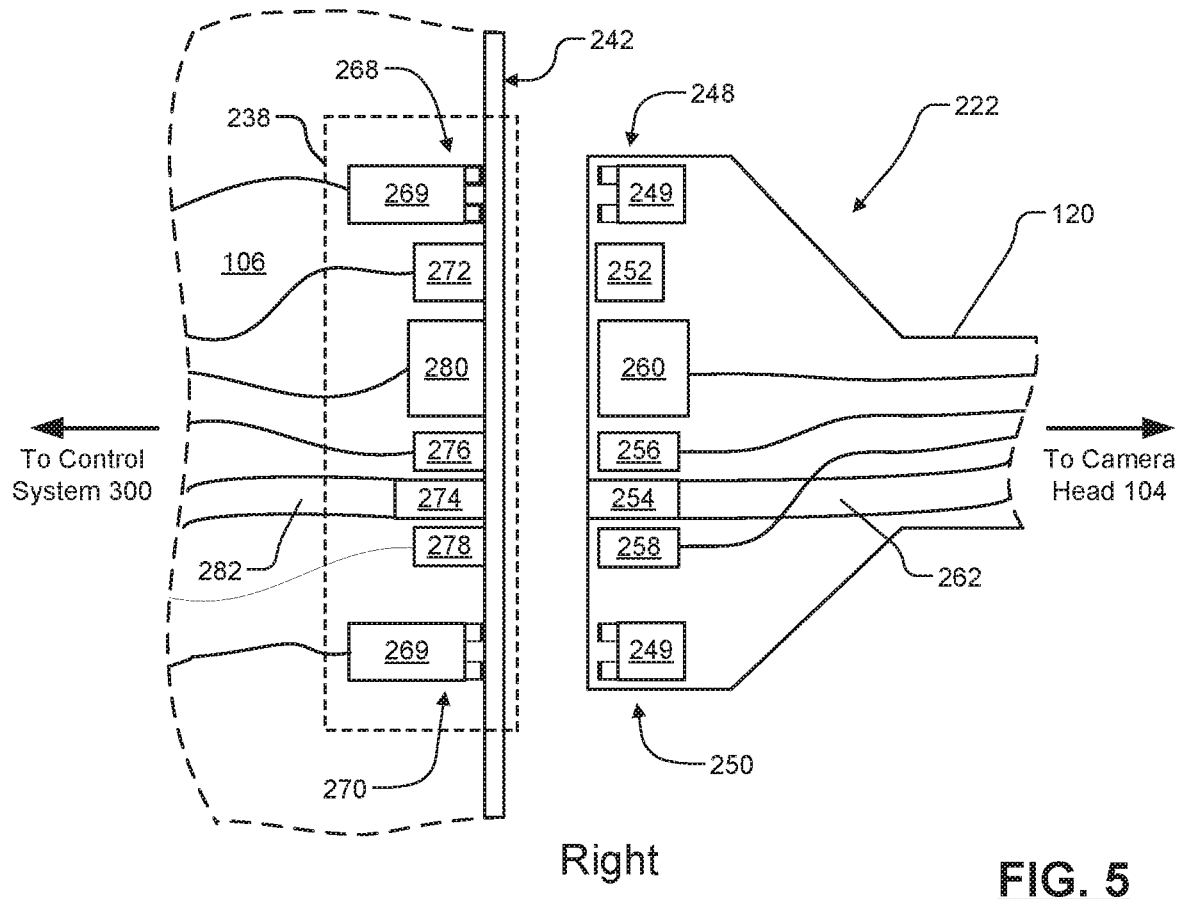
FIG. 5 is a block diagram of the smart coupling system according the principles of the present disclosure.

As shown in FIG. 4 and now FIG. 5, an exemplary set of connection features of the connector 222 includes first connector magnet 248 and second connector magnet 250 on opposite left and right ends of the connector 222. The first connector magnet 248 may include a first polarity and the second connector magnet 250 may include a second polarity. In connector 222, the first polarity may be configured such that a north polarity magnetic field N projects away from the planar surface 242 and the second polarity may be configured such that a south polarity magnetic field S projects away from the planar surface 240. The first polarity and the second polarity may be due to a permanent magnetic polarity, a generated electromagnetic polarity, or a combination of both permanent and electromagnetic. For example, the first connector magnet 248 and/or the second connector magnet 250 may include an electromagnet portion 249 capable of increasing or decreasing the magnetic forces, and in some examples, reversing the polarity of the magnetic fields of the first connector magnet 248 and/or the second connector magnet 250. The electromagnet portions 249 may be powered after coupling with the receptacle 238.

An RFID tag chip 252 may be present in the connector 222. The RFID tag chip 252 may contain electronically stored information related to the attached camera head 104 such as a serial number, software version, firmware version, and compatibility information for use by the input module 106. The RFID tag chip 252 may contain information about features of the camera head 104 The RFID tag chip 252 may be passive and collect energy from a nearby RFID reader using interrogating radio waves. The RFID tag chip 252 may be powered after coupling with the receptacle 238.

The connector 222 further includes one or more transmission/receiving elements for transmitting data, commands, and power to/from the input module 106 via the receptacle 238. For example, the connector 222 may include an optical terminal 254, a wireless transmitter 256, and a wireless receiver 258, and an inductive power receiver 260. Exemplary transmission/receiving elements may be found in the following U.S. Patent Applications, all of which are incorporated by reference herein: U.S. application Ser. No. 15/161,007 filed on May 20, 2016 and Ser. No. 15/598,206 filed on May 17, 2017, both entitled "Apparatus and Method of Providing an Interface to an Electrically Powered Instrument"; Ser. No. 15/598,196 filed on May 17, 2017; Ser. No. 16/012,966 filed on Jun. 20, 2018 and entitled "Medical Scope Device With Improved Radio Frequency Data Interface"; and Ser. No. 15/614,483 filed on Jun. 5, 2017 and entitled "Connector-Based Optical Identification Apparatus and Method"

The optical terminal 254 may be at one end of an optical pathway 262 running up the cable 120 to circuitry within camera head 104. The optical pathway 262 may transmit data to or from the camera head 104. For example, video stream data may be transmitted from an image sensor in the camera head 104 at high data rates supporting 8 k video. Configuration settings and control commands may be transmitted from the input module 106 to the camera head 104. Alternately, the optical pathway 262 may be used to transmit illumination light from a light source (not shown) to light outlet (not shown) on the endoscope 102. Wireless transmitter 256 and wireless receiver 258 may transmit data to or from the camera head 104. For example, video stream data may be transmitted from an image sensor in the camera head 104. Configuration settings and control commands may be transmitted from the input module 106 to the camera head 104. The inductive power receiver 260 may include circuitry for receiving inductive power and controlling an amount of power provided by a transmitter of the input module 106. The power receiver 260 may include circuitry for regulating power to the electromagnetic portions 249 of the first connector magnet 248 and the second connector magnet 250. The power receiver 260 may transmit power to the camera head 104.

The input module 106 may include at the receptacle 238 a set of mating connection features. For example, the receptacle 238 includes first receptacle magnet 268 and second receptacle magnet 270 on opposite left and right ends of the receptacle 238. The first receptacle magnet 268 may include a first polarity and the second receptacle magnet 270 may include a second polarity. In receptacle 238, the first polarity may be configured such that a south polarity magnetic field S projects away from the planar surface 242 and the second polarity may be configured such that a north polarity magnetic field N projects away from the planar surface 242. The first polarity and the second polarity may be due to a permanent magnetic polarity, a generated electromagnetic polarity, or a combination of both permanent and electromagnetic. For example, the first receptacle magnet 268 and/or the second receptacle magnet 270 may include an electromagnet portion 269 capable of increasing or decreasing the magnetic forces, and in some examples, reversing the polarity of the magnetic fields of the first receptacle magnet 268 and/or the second receptacle magnet 270. The electromagnet portions 269 may be powered after coupling with the connector 222.

An RFID reader chip 272 may be present in the receptacle 238. The RFID reader chip 272 may generate interrogating radio waves searching for nearby RFID tag chip 252. RFID reader chip 272 may read the electronically stored information related to the attached camera head 104 such as serial number, software version, firmware version, and compatibility information for use by the input module 106.

The receptacle 238 further includes one or more transmission/receiving elements for transmitting data and commands to/from the camera head 104. For example, the receptacle 238 may include an optical terminal 274, a wireless receiver 276, a wireless transmitter 278, and an inductive power transmitter 280. The optical terminal 274 may be at one end of an optical pathway 282 running to circuitry within the input module 106. The optical pathway 282 may transmit data to or from the camera head 104. For example, video stream data may be transmitted from an image sensor in the camera head 104 at high data rates supporting 8 k video to the input module 106. Configuration settings and control commands may be transmitted from the input module 106 to the camera head 104. Alternately, the optical pathway 282 may be used to transmit illumination light from a light source (not shown) to light outlet (not shown) on the endoscope 102. Wireless receiver 276 and wireless transmitter 278 may transmit data to or from the camera head 104. For example, video stream data may be transmitted from an image sensor in the camera head 104. Configuration settings and control commands may be transmitted from the input module 106 to the camera head 104. The inductive power transmitter 280 may include circuitry for transmitting inductive power and receiving control commands regarding the amount of power to be provided from the inductive power receiver 260.

The connector magnets 248 and 250 and receptacle magnet 268 and 270 may include variable amounts of force between them due to permanent magnetic forces and variable electromagnetic forces. The forces may include attractive levels and repelling levels. These levels may range from approximately 10N-20N but up to more than 30N. For example, pull out forces associated with removing connector 122 from receptacle 138 typically are greater than 30N when applying a force along the axial direction of the connector 122. Therefore, it may be desirable to include comparable permanent or variable magnetic forces.

Figure 6:
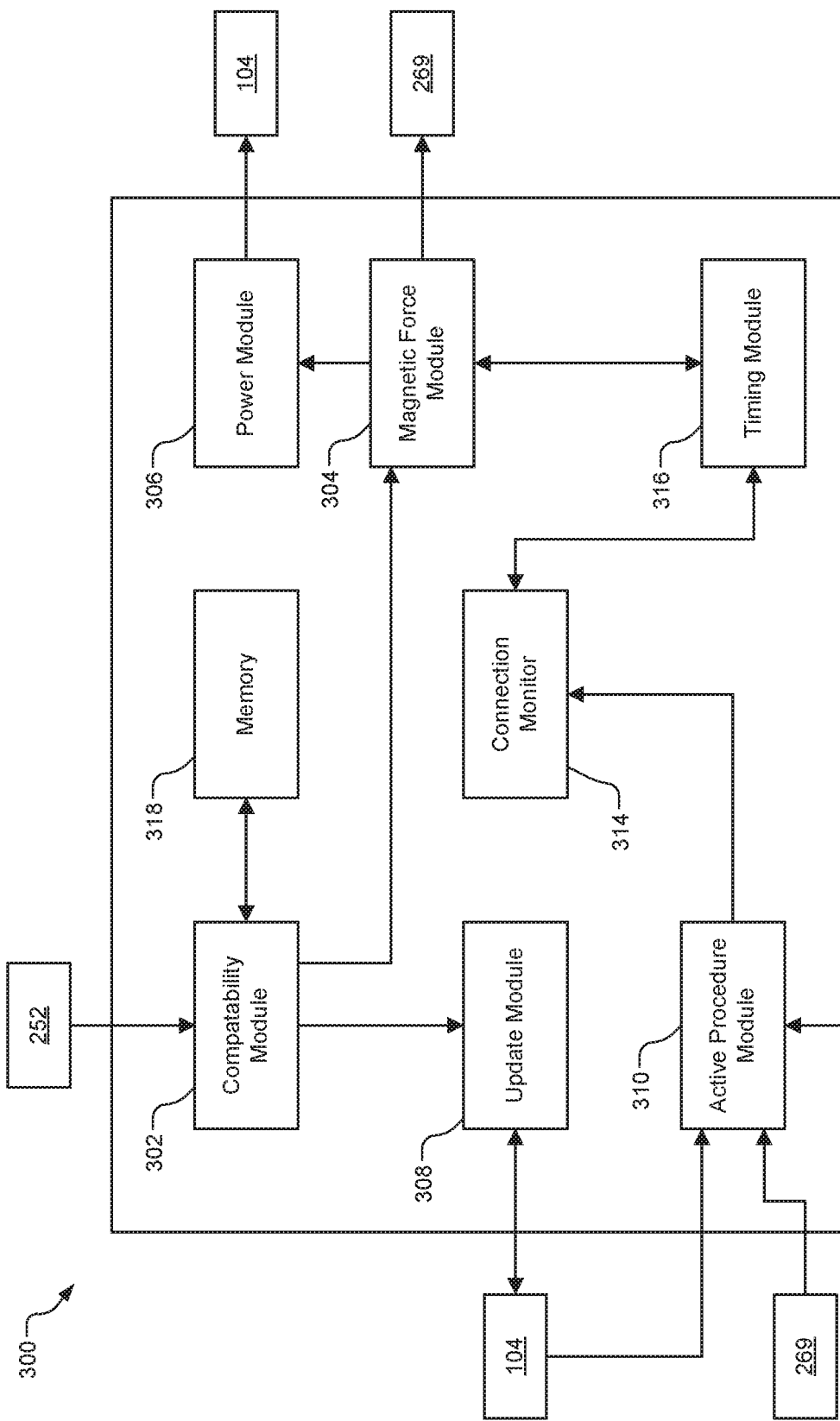
FIG. 6 is a block diagram of a control system of the smart coupling system according to the principles of the present disclosure.

FIG. 6 is a block diagram of an exemplary control system 300 for controlling operation of the connector 222 and receptacle 238. The control system 300 may be embedded within the input module 106. Together, the control system 300, connector 222, and receptacle 238 form a smart coupling system. The control system 300 may include a combination of hardware, firmware, and software for executing a control strategy to actuate electromagnetic portions 249 and 269, the optical receiver 254 and optical transmitter 274, the wireless receivers 258 and 278, the wireless transmitters 256 and 276, and the inductive power receiver 260 and power transmitter 280. The combination of hardware, firmware, and software may be grouped together as modules of the control system 300.

Continuing with FIG. 6, the control system 300 may include a compatibility module 302, a magnetic force module 304, a power module 306, an update module 308, an active procedure module 310, user input 312, connection monitor 314, and a timing module 316. When the connector 222 is brought into contact with or in close proximity to the receptacle 238, the RFID reader chip 272 may cause the RFID tag chip 252 to transmit information about the attached device (endoscope 102 and/or camera head 104). The compatibility module 302 may receive the information about the attached device from the RFID reader chip 272 and compare the information with compatibility data stored in memory 318.

The magnetic force module 304 may generate a magnetic force signal to increase, decrease, or reverse polarity of the electromagnet portions 269. The magnetic force module 304 may cause the current to increase or decrease to coils of the electromagnet portions 269. The magnetic force module 304 may cause the current to reverse as well. If an incompatible device is connected, the magnetic force module 304 may disable the electromagnetic force between the connector 222 and receptacle 238. In addition, the magnetic force module 304 may reverse the polarity of the electromagnet portions 269 and set the electromagnetic force level to a first repelling level to repel the connection. The operator may be notified of the incompatibility and prompted to disconnect the connector 222 prior to reversing the polarity. The first repelling level may include a repelling force greater than the force due to the permanent magnetic force between the magnets 248/250 and 268/270 respectively. The first repelling level may be a force greater than 10N. If a compatible device is connected, the magnetic force module 304 may set the electromagnetic force between the connector 222 and receptacle 238 to a first attractive level that is greater than the permanent magnetic force between the magnets 248/250 and 268/270 respectively. The first attractive level may be a force greater than 10N. After the first attractive level is reached, the magnetic force module 304 may initiate the power module 306 to provide inductive power to the inductive power transmitter 280. Electrical power may then be transmitted to the inductive power receiver 260 to power the camera head 104.

The camera head 104 may include software, firmware, memory, and a processor for operating the image sensor and other circuitry. The update module 308 may request that the camera head 104 provide information about the software or firmware version to determine whether an update is needed. The update module 308 may compare the current version of the software or firmware with known versions available on the input module 106, a stored memory drive, a network server, etc. to determine if an update is required. If an update is required, the update module 308 may initiate the update or, in the alternative may indicate to the user that an update is recommended or required prior to operation of the system.

The active procedure module 310 monitors the input module 106 to determine whether a surgical procedure has been selected and/or whether the surgical procedure is active. For example, user input 312 may be provided by the operator by selecting a surgical procedure from a menu or by beginning imaging using the camera head 104. The active procedure module 310 may generate a procedure-selected signal. Once the surgical procedure is selected, the active procedure module 310 may monitor sensors in the camera head 104 such as IMUs or accelerometers or image data to determine whether the surgical procedure is active, and if so generate a procedure active signal.

The magnetic force module 304 may monitor the procedure selected signal and the procedure active signal to adjust the magnetic force signal. For example, the magnetic force module 304 may increase the electromagnetic force to a second attractive level greater than the first attractive level once a procedure has been selected based on the procedure-selected signal. The second attractive level may be approximately 30N. The magnetic force module 304 may increase the electromagnetic force to a third attractive level greater than the second attractive level once a procedure is active based on the procedure active signal. The third attractive level may be approximately 40N. If the procedure is no longer active or selected, the magnetic force module 304 may decrease the electromagnetic force to the second attractive level, the first attractive level, or turn it off accordingly. In addition, if the operator indicates via user input that the procedure has ended, the magnetic force module 304 may decrease or turn off the electromagnetic force. Although first, second, and third attractive levels of magnetic force are disclosed above, one skilled in the art would understand the need for additional levels as needed.

The system 300 is intended to provide an amount of electromagnetic force to maintain connection of the connector 222 and receptacle 238 that is at least as great as the forces between ordinary connector 122 and receptacle 138. However, an accidental disconnect may occur. The connection monitor 314 determines when an accidental disconnect occurs based on the procedure selected signal, procedure active signal, user input, and image data. In some examples, the connection monitor 314 may receive force feedback from the magnetic force module 304 based on a change in flux of the inductive coils. If an accidental disconnect is detected, the connection monitor 314 may send a disconnect signal to the magnetic force module 304 and initiate the timing module 316 to start a timer. The magnetic force module 304 may decrease the electromagnetic force to the first attractive level or alternatively turn off the electromagnetic force. If the timer exceeds a threshold time and the connection monitor 314 does not detect a reconnect, the connection monitor 314 sends a reset signal to the compatibility module 302. If the connection monitor 314 detects a reconnect and the timer is less than or equal to the threshold time, the connection monitor 314 sends a bypass signal to the compatibility module 302 and a reconnect signal to the magnetic force module 304. The magnetic force module 304 may increase the electromagnetic force to the first attractive level and then the second attractive level.

Figure 7:
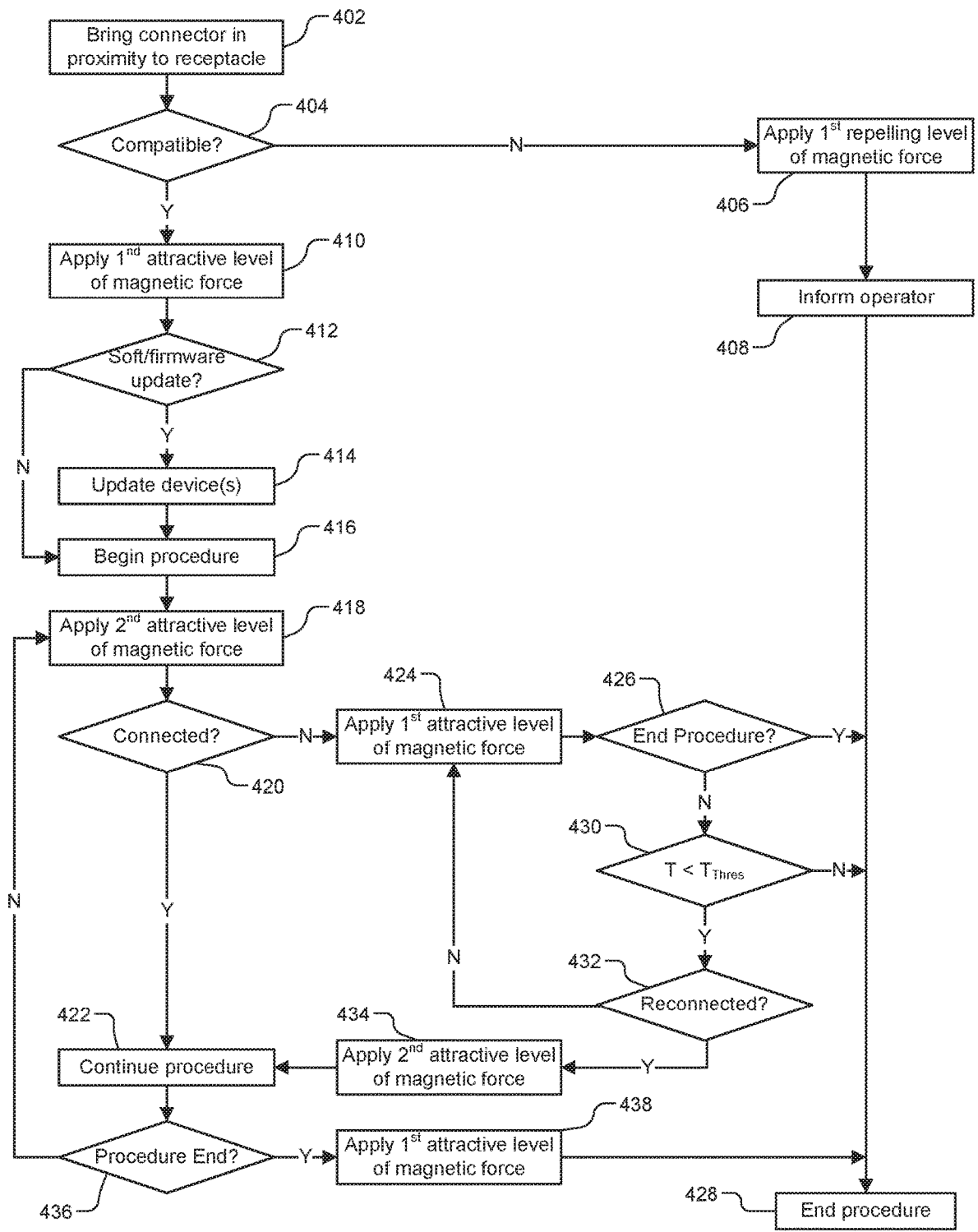
FIG. 7 is a flowchart illustrating steps executed for controlling the smart coupling system according to the principles of the present disclosure.

FIG. 7 includes a flow chart 400 that illustrates steps the control system 300 may take to control the coupling of connector 222 and receptacle 238. In step 402, the operator brings the connector 222 in proximity to the receptacle 238. At step 404, the compatibility module 302 quickly determines whether the connector 222 attached to the camera head 104 is compatible with the input module 106. If not compatible, the magnetic force module 304 creates a first repelling level of magnetic force in step 406. The input module 106 may also inform the operator of the incompatibility in step 408. If compatible, the magnetic force module 304 creates a first attractive level of magnetic force in step 410. Power may then be supplied via the inductive power transmitter 280 and power receiver 260.

In step 412, the update module 308 checks software and/or firmware in the camera head 104 to determine if an update is needed. If so, the camera head 104 receives updates at step 414. If no update is necessary, the operator may begin the procedure at step 416 by selecting a procedure or activating the imager of the camera head 104. The magnetic force module 304 increases power to the electromagnetic portions 269 to the second attractive level of magnetic force at step 418.

At step 420, the connection monitor 314 determines whether the connector 222 is connected with the receptacle 238. If so, the procedure continues at step 422. If a disconnect occurs, the magnetic force module 304 lowers power to the electromagnetic portions 269 to the first attractive level at step 424. This may be done to make recoupling of the connector 222 with the receptacle easier or less abrupt. At step 426, the active procedure module 310 determines whether the procedure is still active. For example, if the operator has ended the procedure by powering off the camera head 104 or selecting to end the procedure, the procedure ends at step 428. If the procedure is still active, the timing module 316 begins incrementing the timer and checks to see if the timer T is less than a threshold time $T_{Thres}$ at step 430. If the timer has exceeded the threshold time, the procedure ends at step 428.

While the timer T is less than the threshold time $T_{Thres}$, the connection monitor 314 checks the receptacle 238 to determine if a reconnect has occurred at step 432. When no reconnect occurs, the magnetic force module 304 continues to apply the first attractive level of magnetic force at step 424 and proceeds to continue to check for a reconnect. If a reconnect has occurred, the magnetic force module 304 applies the second attractive level of magnetic force at step 434. The procedure then continues at step 422. The operator may choose to end the procedure at step 436. If the procedure has ended, the magnetic force module 304 applies the first attractive level of magnetic force at step 438 and the procedure ends at step 428. If the procedure has not ended, the magnetic force module 304 continues to apply the second attractive level of magnetic force at step 418.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A control system for a coupling an input device and an input module of an imaging system for a medical procedure; comprising:
    a compatibility module that generates a compatibility signal indicating the input device is compatible with the input module or indicating that the input device is incompatible with the input module based on electronic information stored on the input device;
    a magnetic force module that generates an electromagnetic force between a connector of the input device and a receptacle of the input module based on the compatibility signal,
    wherein the magnetic force module applies a first attractive level of the electromagnetic force when the compatibility signal indicates compatible and a first repelling level of the electromagnetic force when the compatibility signal indicates incompatible; and
    an active procedure module that generates an active procedure signal indicating the medical procedure is active or indicating the medical procedure is no longer active based on at least one of a user input and image data generated by the input device,
    wherein the magnetic force module applies a second attractive level that is greater than the first attractive level when the active procedure signal indicates active.

2. The control system of claim 1, further comprising:
    a connection monitor that generates a connection signal indicating the connector and the receptacle are in a connected state or the connector and the receptacle are in a disconnected state,
    wherein the magnetic force module applies the first attractive level when the connection signal indicates the disconnected state and the active procedure module indicates active, and
    wherein the magnetic force module continues to apply the second attractive level when the connection signal indicates the connected state and the active procedure module indicates active.

3. The control system of claim 2, further comprising:
    a timing module that increments a timer when the connection signal indicates the disconnected state and the active procedure module indicates active,
    wherein the magnetic force module continues to apply the first attractive level while the timer is less than a predetermined threshold and the connection signal indicates the disconnected state,
    wherein the magnetic force module increases from the first attractive level to the second attractive level while the timer is less than the predetermined threshold and the connection signal indicates the connected state.

4. The control system of claim 1, wherein the compatibility module includes an RFID reader chip and the electronic information is stored on an RFID tag chip of the connector such that the RFID reader chip powers the RFID tag chip using radio wave energy to transmit electronic information.

5. The control system of claim 1, wherein the input device is one of a video camera for an endoscope and a video endoscope.

6. A coupling system for coupling an input device and an input module of a medical imaging system, comprising:
    a connector at a terminal end of a cable of the input device that includes one or more connector magnets and an RFID tag chip, the connector terminating in a planar surface without exposed terminals;
    a receptacle within the input module that includes one or more receptacle magnets and an RFID reader chip, the receptacle terminating in a planar surface without exposed terminals; and
    a control system including
        a compatibility module that generates a compatibility signal indicating the input device is compatible with the input module or indicating that the input device is incompatible with the input module based on electronic information stored on the RFID tag chip; and
        a magnetic force module that generates an electromagnetic force in the one or more receptacle magnets based on the compatibility signal,
        wherein the magnetic force module applies a first attractive level of the electromagnetic force when the compatibility signal indicates compatible and a first repelling level of the electromagnetic force when the compatibility signal indicates incompatible; and
        an active procedure module that generates an active procedure signal indicating the medical procedure is active or indicating the medical procedure is no longer active based at least one of a user input and on image data generated by the input device,
        wherein the magnetic force module applies a second attractive level that is greater than the first attractive level when the active procedure signal indicates active.

7. The coupling system of claim 6, further comprising:
    a connection monitor that generates a connection signal indicating the connector and the receptacle are in a connected state or the connector and the receptacle are in a disconnected state,
    wherein the magnetic force module applies the first attractive level when the connection signal indicates the disconnected state and the active procedure module indicates active, and
    wherein the magnetic force module continues to apply the second attractive level when the connection signal indicates the connected state and the active procedure module indicates active.

8. The coupling system of claim 7, further comprising:
    a timing module that increments a timer when the connection signal indicates the disconnected state and the active procedure module indicates active,
    wherein the magnetic force module continues to apply the first attractive level while the timer is less than a predetermined threshold and the connection signal indicates the disconnected state, wherein the magnetic force module increases from the first attractive level to the second attractive level while the timer is less than the predetermined threshold and the connection signal indicates the connected state.

9. The coupling system of claim 6, wherein the input device is one of a video camera for an endoscope and a video endoscope.

* * * * *